United States Patent

Gray et al.

[11] Patent Number: 6,086,008
[45] Date of Patent: Jul. 11, 2000

[54] APPARATUS AND METHOD FOR PERMITTING INTRODUCTION AND WITHDRAWAL OF A CATHETER

[75] Inventors: Larry B. Gray, Merrimack; Dean L. Kamen, Bedford, both of N.H.

[73] Assignee: DEKA Products Limited Partnership, Manchester, N.H.

[21] Appl. No.: 09/218,790

[22] Filed: Dec. 21, 1998

Related U.S. Application Data

[60] Provisional application No. 60/068,383, Dec. 22, 1997.

[51] Int. Cl.[7] .......................... B65H 75/38; A61M 5/178; A61M 25/01; A61F 11/00
[52] U.S. Cl. ...................... 242/388.6; 604/159; 604/528; 606/108
[58] Field of Search ................................. 242/388.6, 603; 604/159, 528; 606/108

[56] References Cited

U.S. PATENT DOCUMENTS

| | | | |
|---|---|---|---|
| 3,561,445 | 2/1971 | Katerndahl et al. | 128/214.4 |
| 4,160,451 | 7/1979 | Chittenden | 128/214.4 |
| 4,342,313 | 8/1982 | Chittenden | 128/214.4 |
| 4,397,091 | 8/1983 | Gustavsson et al. | 33/127 |
| 4,616,648 | 10/1986 | Simpson | 128/303 R |
| 4,713,059 | 12/1987 | Bickelhaupt et al. | 604/171 |
| 4,850,974 | 7/1989 | Bickelhaupt et al. | 604/171 |
| 4,903,826 | 2/1990 | Pearce | 206/63.3 |
| 4,917,094 | 4/1990 | Lynch et al. | 128/657 |
| 5,135,535 | 8/1992 | Kramer | 606/194 |
| 5,441,055 | 8/1995 | Ales et al. | 128/772 |
| 5,454,785 | 10/1995 | Smith | 604/49 |
| 5,464,023 | 11/1995 | Viera | 128/772 |
| 5,690,617 | 11/1997 | Wright | 604/179 |
| 5,690,645 | 11/1997 | Van Erp | 606/108 |
| 5,707,363 | 1/1998 | Crawford et al. | 604/165 |
| 5,730,150 | 3/1998 | Peppel et al. | 128/772 |
| 5,769,222 | 6/1998 | Banerian | 206/364 |
| 5,827,202 | 10/1998 | Miraki et al. | 600/585 |
| 5,843,002 | 12/1998 | Pecor et al | 600/585 |

FOREIGN PATENT DOCUMENTS 2215703A  9/1989  United Kingdom.

*Primary Examiner*—John Q. Nguyen
*Attorney, Agent, or Firm*—Bromberg & Sunstein LLP

[57] ABSTRACT

A catheter reel apparatus facilitating one-person, single-handed control of catheter movement along a guidewire is provided in an embodiment. In a preferred embodiment, the reel has two grooves of different dimensions. The first groove is sized to carry a portion of the guidewire not within a catheter lumen while the second groove is sized to carry a portion of the catheter, which has the guidewire inserted in the lumen. As the reel is rotated, the proximal end of the catheter is deployed from the device through an exit provided by a housing. Continued rotation pays out the desired length of catheter and the catheter is guided, without guidewire moving into or out of the housing, to a desired location. When the catheter is to be withdrawn, the reel is rotated in the opposite sense to catheter deployment.

11 Claims, 11 Drawing Sheets

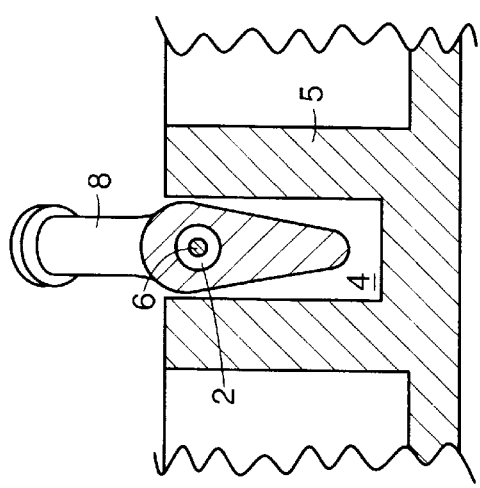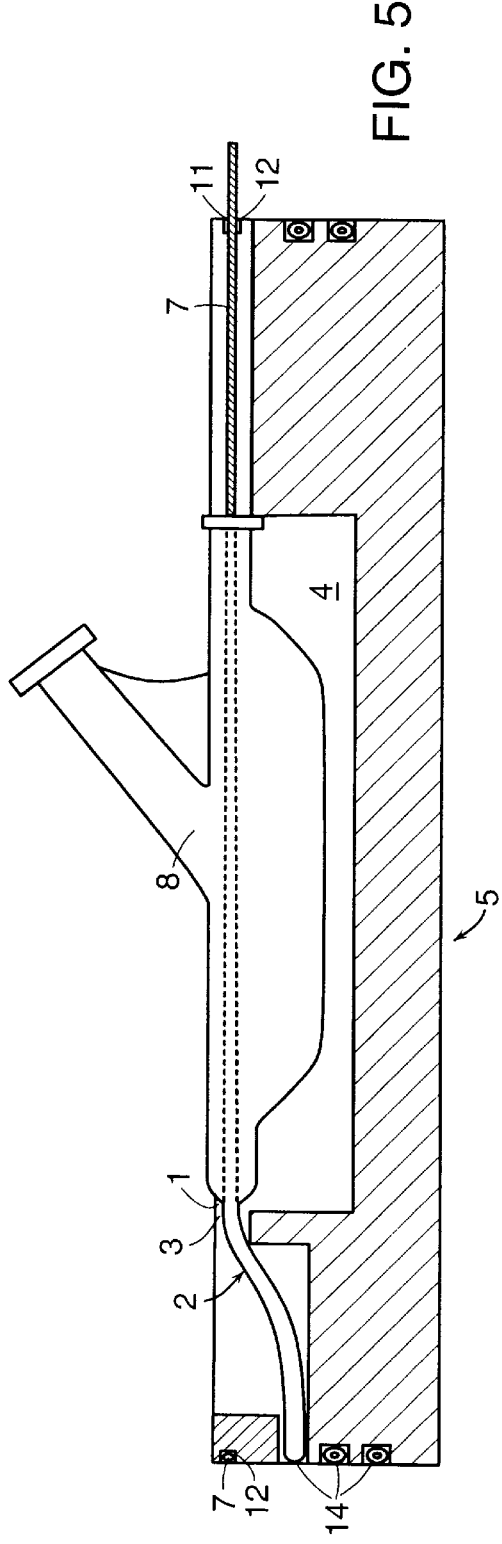

APPARATUS AND METHOD FOR PERMITTING INTRODUCTION AND WITHDRAWAL OF A CATHETER

RELATED U.S. APPLICATION

The present application claims priority from Provisional Application Ser. No. 60/068,383, filed Dec. 22, 1997, which is hereby incorporated herein by reference.

TECHNICAL FIELD

The present invention relates to methods and devices designed for controlling the movement of catheters useful in many medical procedures. In particular, an apparatus to facilitate one-person, single-handed control of a catheter moved along a guidewire is disclosed.

BACKGROUND ART

Catheters are routinely introduced into blood and other vessels of a subject during numerous medical procedures. In some procedures, accurate placement within vessels is important and desirable. Generally, guidewires are first inserted into the vessel so that an end is at the position to be treated. Catheters are provided with a suitable lumen into which the other guidewire end is inserted and the catheter is slid over the guidewire to the position.

In some circumstances, it may desirable to insert a first catheter to a location, perform a procedure, withdraw the first catheter and exchange it with a second catheter to be placed at the same location. An example of such a circumstance is a procedure to open a stenosis by utilizing a series of balloon dilatation catheters which have different sized balloons.

In addition to difficulties associated with accurate, reproducable catheter placement, handling and manipulation of the catheters in an operating room environment can become unwieldy. Some methodologies require more than one person to successfully perform. The need for maintaining sterility, particularly during the exchange of catheters, is of concern.

SUMMARY OF THE INVENTION

The invention provides a catheter reel apparatus facilitating one-person, single-handed control of catheter movement along a guidewire. The apparatus includes a reel, having a groove and being held within a housing. A guidewire having greater overall length than the catheter is inserted in a lumen of the catheter. In a preferred embodiment, the reel has two grooves of different dimensions. The first groove is sized to carry a portion of the guidewire that is not within the catheter lumen. The second groove is sized to carry a portion of the catheter, which has the guidewire inserted in its lumen. The grooves are preferably shaped and sized to minimize radial and axial movement of the guidewire with respect to the reel when the reel is not being turned. As the reel is rotated, the proximal end of the catheter is deployed from the device through an exit provided by the housing. Continued rotation pays out the desired length of catheter. The distal terminus of the guidewire is anchored to the housing during reel rotation. Thereby, the catheter is guided, without guidewire moving into or out of the housing, to a desired location.

In accordance with one embodiment of the invention, there is provided an arrangement for engaging the catheter with the reel. A connecting passage, having a proximal opening and a distal opening and defined by the reel, permits the catheter, which extends outwardly from the proximal opening, to occupy the second groove, while permitting the portion of the guidewire lying outside the catheter to occupy the first groove. The passage may be designed to hold a commercially available Y-fitting.

The apparatus may include a fastener to removably affix a second wire to the guidewire. The second wire may be pre-placed with its proximal terminus at a defined site (within the patient) from which movement is undesirable. The catheter may be deployed along the length of both wires without further movement of either wire so long as the fastener is able to pass through the lumen.

The rim is rotated to deploy the catheter while the guidewire remains fixed. This is a one-handed operation facilitated by turning the reel using an accessible knob. The catheter is deployed as the knob is rotated until the proximal end of the catheter reaches the location. In a preferred embodiment, the reel is impeded from rotating past a position for which the catheter is in the desired position. When the catheter is to be withdrawn, the knob is rotated in the opposite sense to deployment until the catheter is, again, wrapped on the reel.

BRIEF DESCRIPTION OF THE DRAWINGS

FIG. 4 is a cross-section through line A—A of the Y-fitting of FIG. 3.

FIG. 5 is a longitudinal section of the catheter reel in the region of the connecting passage according to a specific embodiment of the invention.

DESCRIPTION OF SPECIFIC EMBODIMENTS OF THE INVENTION

The apparatus includes a catheter reel and a housing for the reel. The reel may be rotated within the housing thereby deploying a catheter. The catheter is initially wrapped around the circumference of the reel. A guidewire inserted in a catheter lumen defines the path of catheter deployment away from the reel. One end of the apparatus's guidewire— or of a second wire (i.e., a guidewire within the patient's body) that is later fastened to the apparatus's guidewire—may be placed at a precise location within the body of a patient (for example, within the cardiovascular system) requiring surgical intervention. Use of the apparatus allows the catheter to be deployed to the precise location. The end of the catheter directed toward the location is denoted the proximal end, while the end remaining on the reel is the distal end. The terms "proximal" and "distal" are also used in describing the orientation of the other elements related to the apparatus. During or after completion of a surgical procedure, the apparatus permits withdrawal of the catheter and the rewrapping of its length upon the reel. Use of a replacement apparatus would allow a new catheter to be deployed to the same location.

Figure 1:
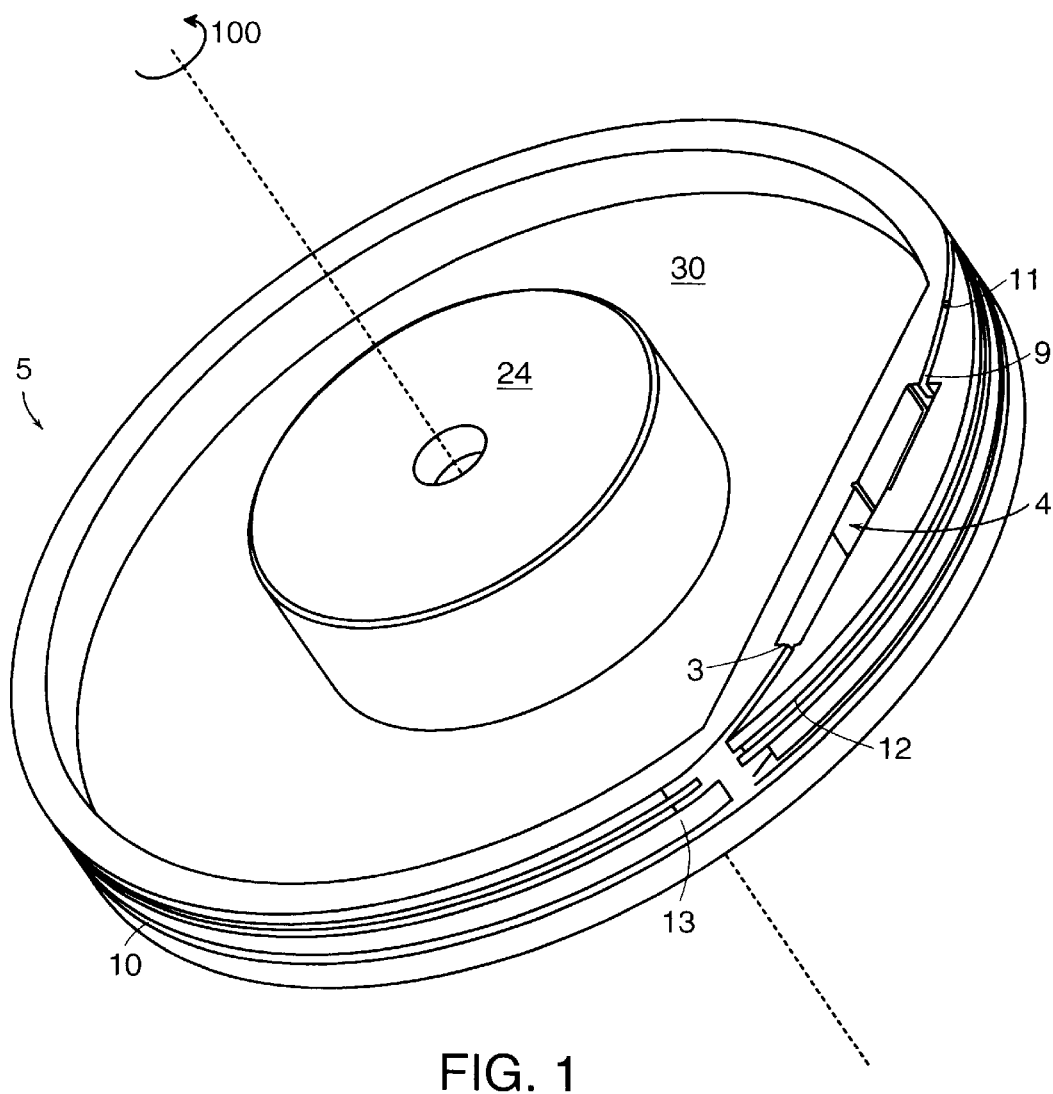
FIG. 1 is a perspective view of a catheter reel according to an embodiment of the invention.
Figure 2:
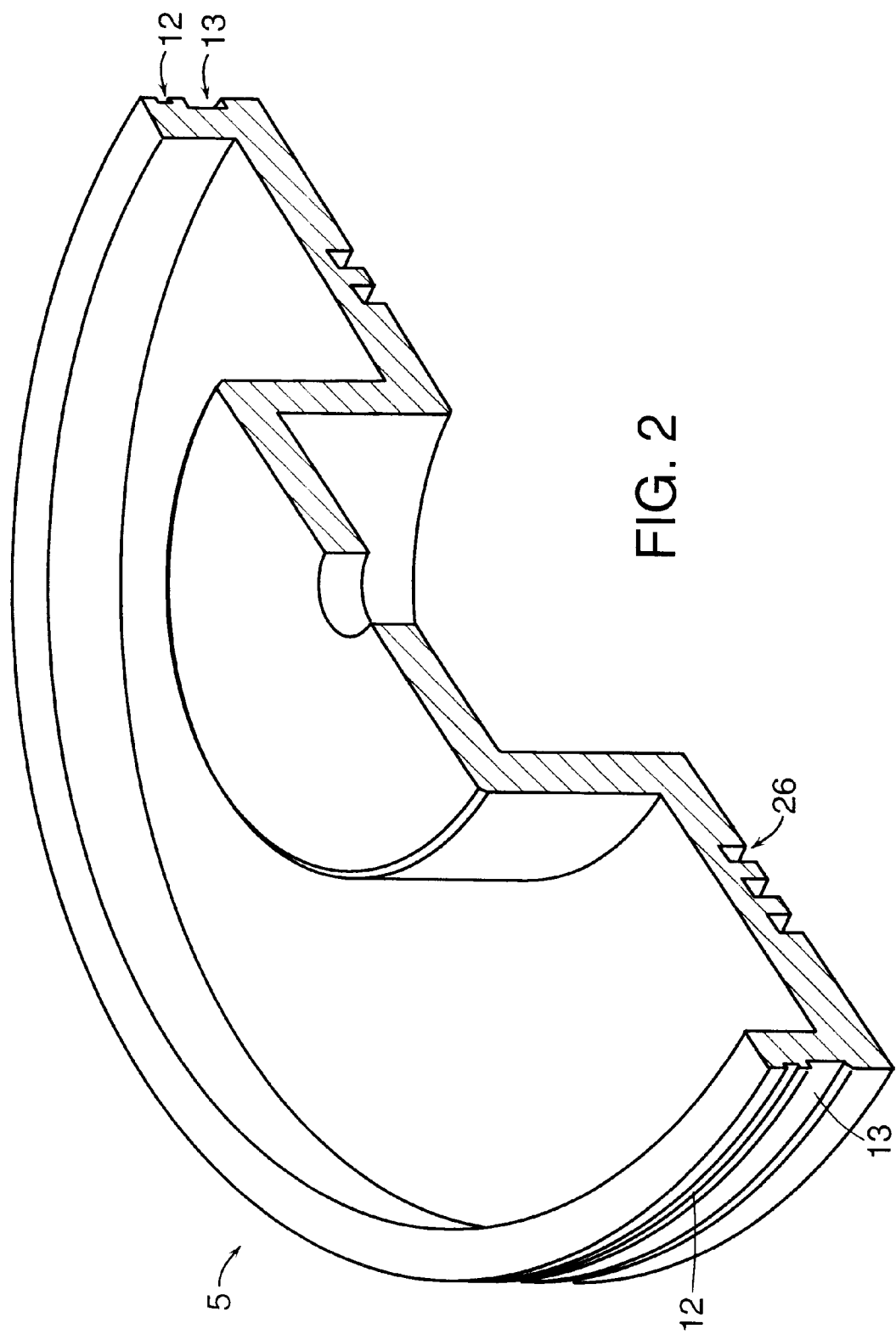
FIG. 2 is a cutaway view of the catheter reel of FIG. 1.

The distal end 1 of a catheter 2 (items 1 and 2 first shown in FIGS. 3 and 5 below) is placed at the proximal opening 3 of a connecting passage 4 defined by a catheter reel 5 as shown in FIG. 1. As shown below in FIG. 4, the catheter 2 has disposed within it a lumen 6 which may contain a guidewire 7 inserted therein (item 7 first shown in FIGS. 3 and 5.) FIG. 1 shows a particular embodiment of a catheter reel 5 in which the connecting passage 4 is shaped to hold a commercially available Y-fitting (shown as item 8 in FIGS. 3–5 below). When in place the guidewire 7 extends distally from the distal opening 9 of the connecting passage 4 and passes through the guidewire exit 11. The catheter reel 5, in an embodiment, has a groove disposed on its rim 10. In a preferred embodiment as shown in FIG. 1, the reel 5 has two distinct grooves disposed on rim 10. A first groove 12 is dimensioned to carry the portion of the guidewire 7 that lies outside of the lumen 6. A second groove 13 is dimensioned to carry the catheter 2 which extends from the proximal opening 3 into the second groove 13. The first and second grooves are preferably dimensioned so that the guidewire 7 remains the same distance away from the axis of reel rotation 100 regardless of whether the guidewire 7 is in the lumen 6 (occupying the second groove 13) or outside of the lumen 6 (occupying the first groove 12). Before commencing operation of the apparatus, the catheter 2 is wrapped around the reel 5 occupying the second groove 13. FIG. 1 also depicts a knob 24 affixed to a top face 30 of reel 5. FIG. 2 shows a cutaway view of the catheter reel 5 of FIG. 1 illustrating the first groove 12 for carrying guidewire and the second groove 13 for carrying the catheter.

Figure 3:
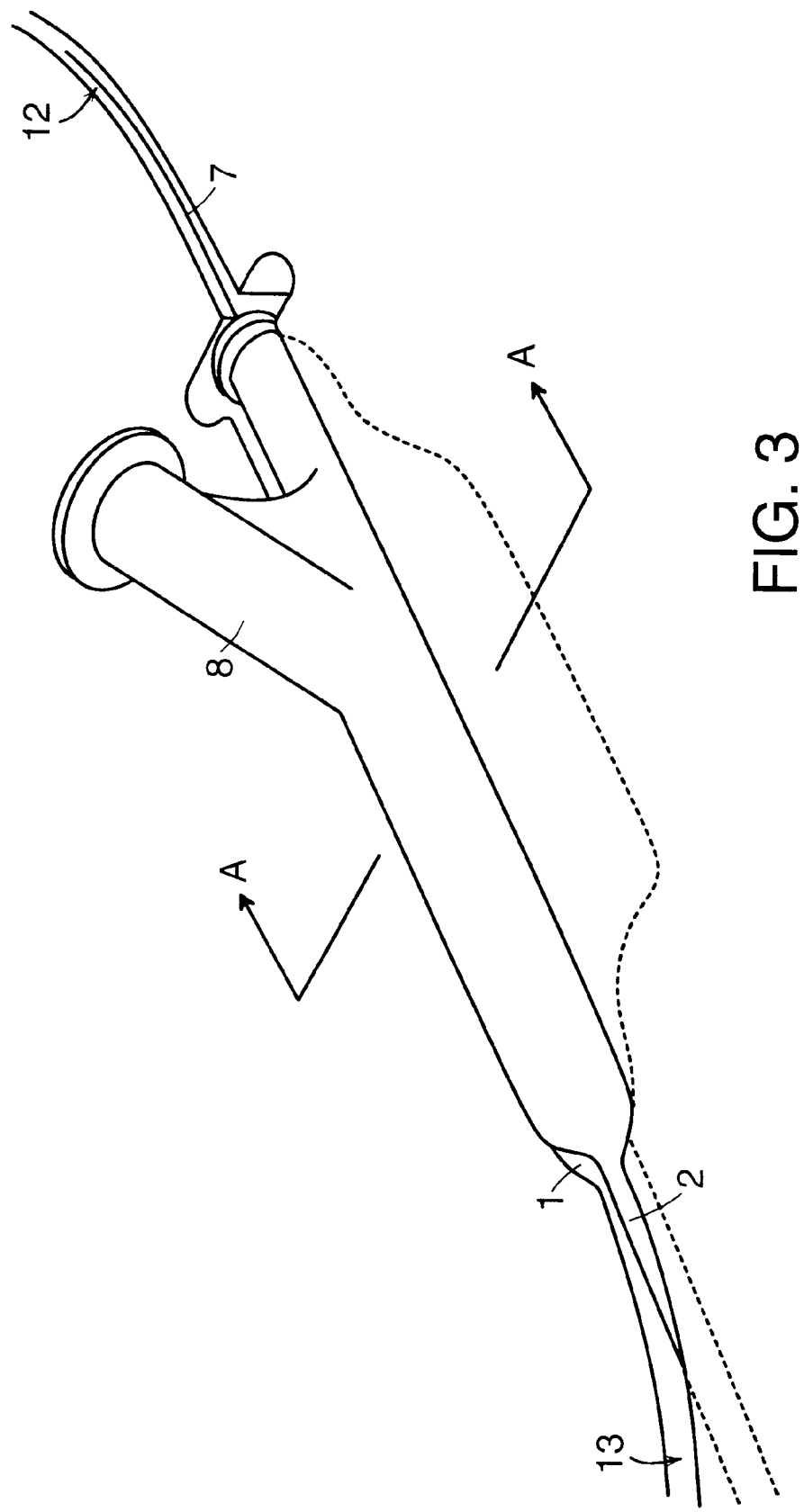
FIG. 3 shows a Y-fitting installed in a catheter reel according to a specific embodiment of the invention.

FIG. 3 shows, for a particular embodiment, the Y-fitting 8, the guidewire 7 extending distally and occupying the first groove 12, and the catheter 2 extending proximally. FIG. 4 further details, in cross-sectional view, the Y-fitting 8 occupying the connecting passage 4.

FIG. 5 is a longitudinal section of the portion of the catheter reel 5 containing the connecting passage 4. FIG. 5 illustrates a preferred embodiment to accommodate catheter length of greater than one reel circumference. In this embodiment, a catheter 2, occupying three segments of a continuous helical second groove 14, is depicted. (Alternatively, as shown in FIGS. 1 and 2, a single groove 13 wide enough to hold three wraps of the catheter 2 may be used instead of a helical groove 14. Thus, overlapping catheter portions may occupy the second groove 13 simultaneously.

Figure 6A:
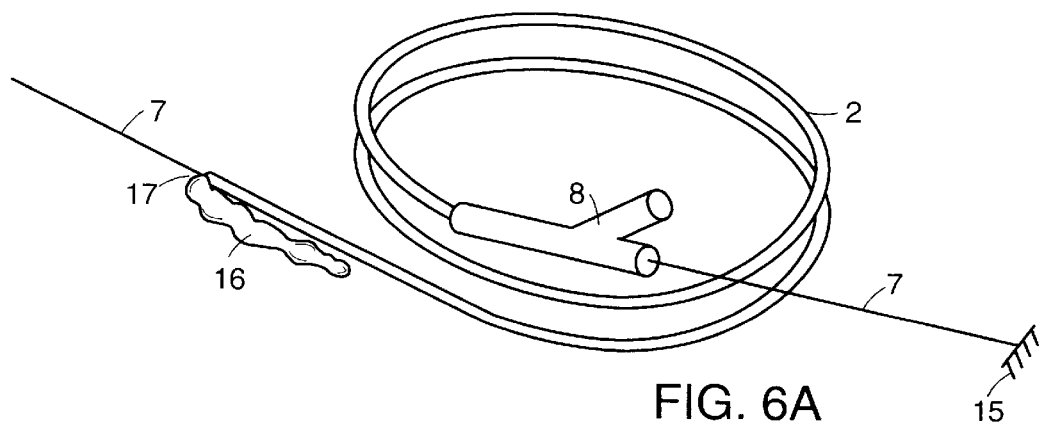
FIGS. 6A, 6B, and 6C show, sequentially, how the catheter is deployed along the guidewire according to an embodiment of the invention.
Figure 6B:
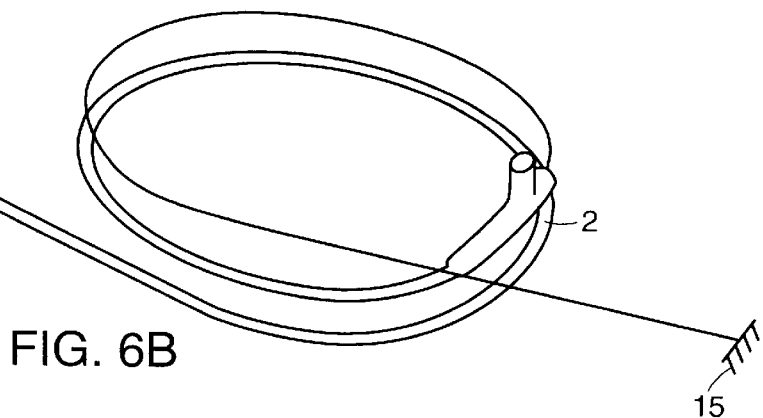
Figure 6C:
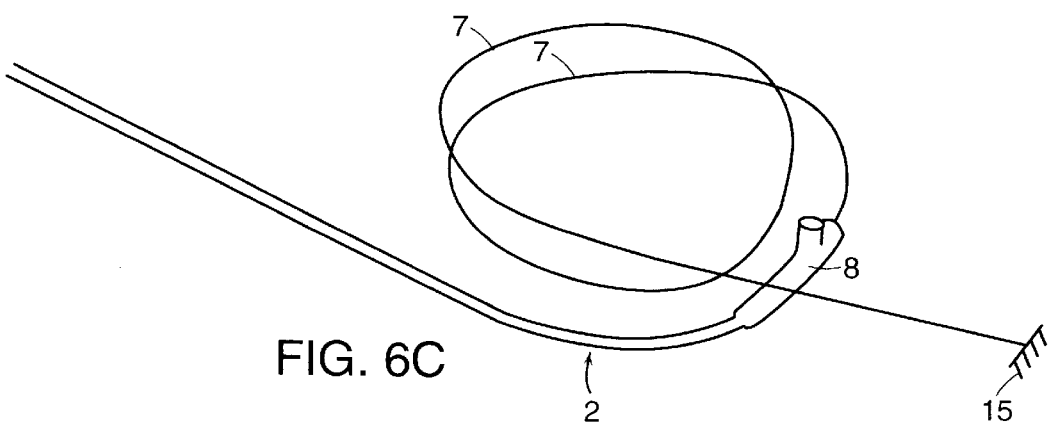

In a particular embodiment of the invention, the distal portion of guidewire 7 extends through the guidewire exit 11 and into the first groove 12 and is rigidly held by an anchor 15 (shown schematically in FIGS. 6A, 6B, 6C below) to a housing 18 (shown in FIG. 7 below). There should be no movement of the guidewire 7 into or out of housing 18 while reel 5 is rotated and the catheter 2 is deployed. Such undesirable movement might adversely affect the accuracy of placement of the proximal portion of guidewire 7. The dimensions of first groove 12 and second groove 13 are, in this preferred embodiment, sized so as to insure that guidewire slack as well as any other guidewire and catheter movement other than that in the direction and plane of deployment are minimized. FIGS. 6A, 6B, and 6C depict progressive deployment of the catheter 2. FIG. 6A shows catheter 2 completely stowed. It also illustrates the position of an angioplasty balloon 16 affixed near the proximal end 17 of the catheter 2. FIG. 6B shows an intermediate state of catheter 2 payout, while FIG. 6C shows complete deployment of catheter 2 and further represents guidewire 7 configuration at that stage of operation.

Figure 7:
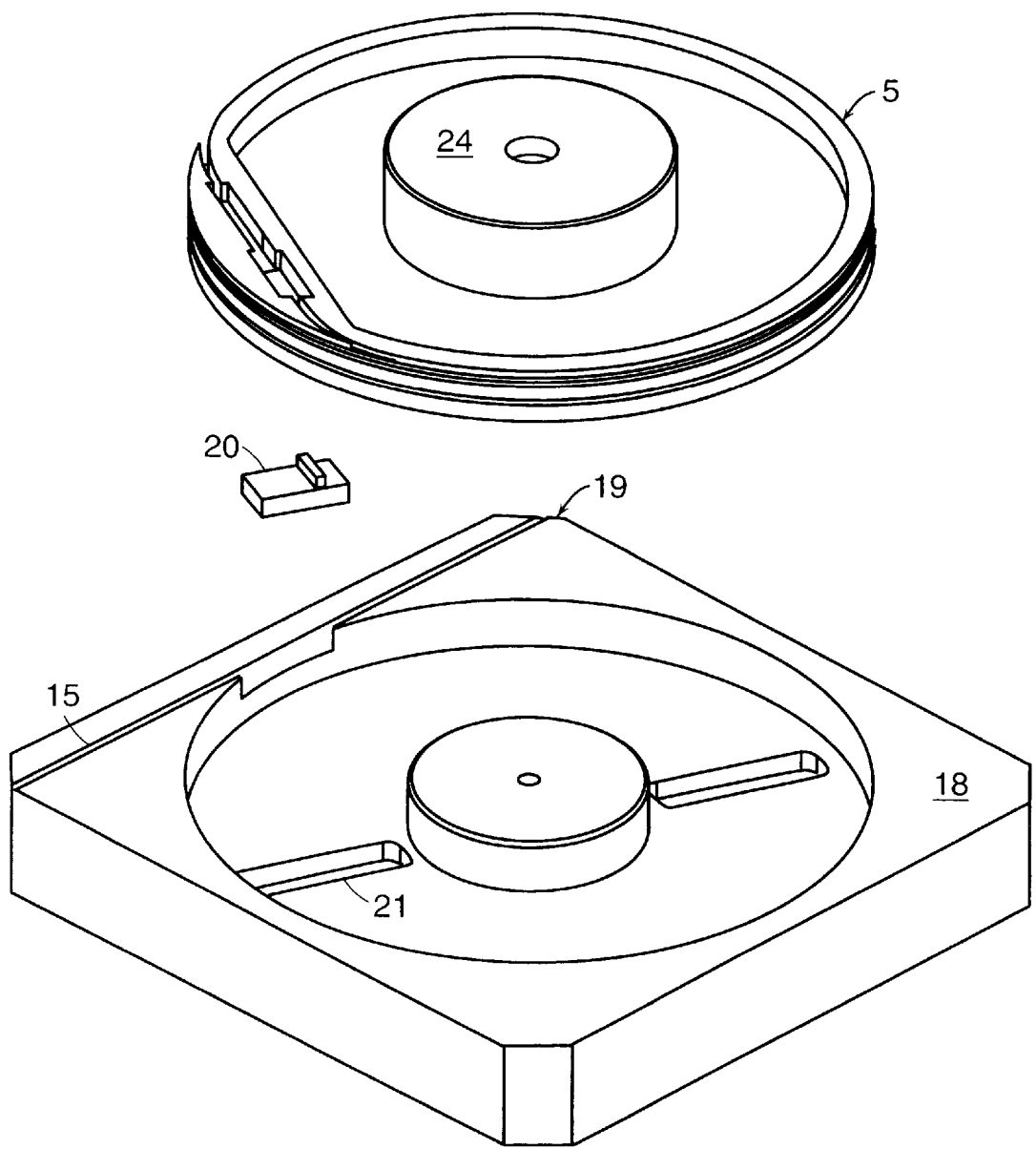
FIG. 7 is an exploded view of a catheter reel and a housing according to an embodiment of the invention.
Figure 8:
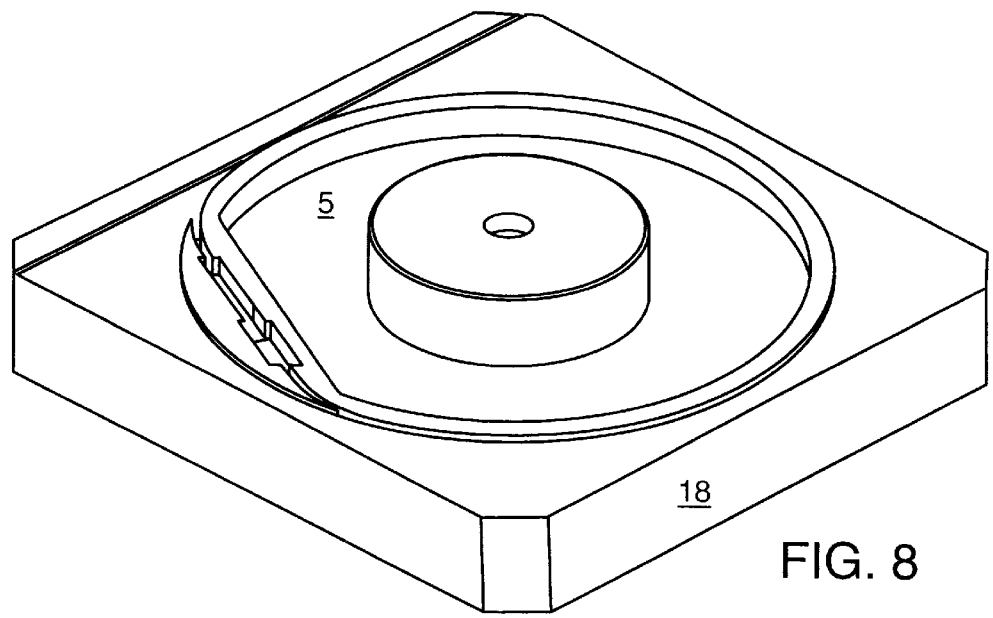
FIG. 8 is a perspective view showing assemblage of a catheter reel within a housing.
Figure 10:
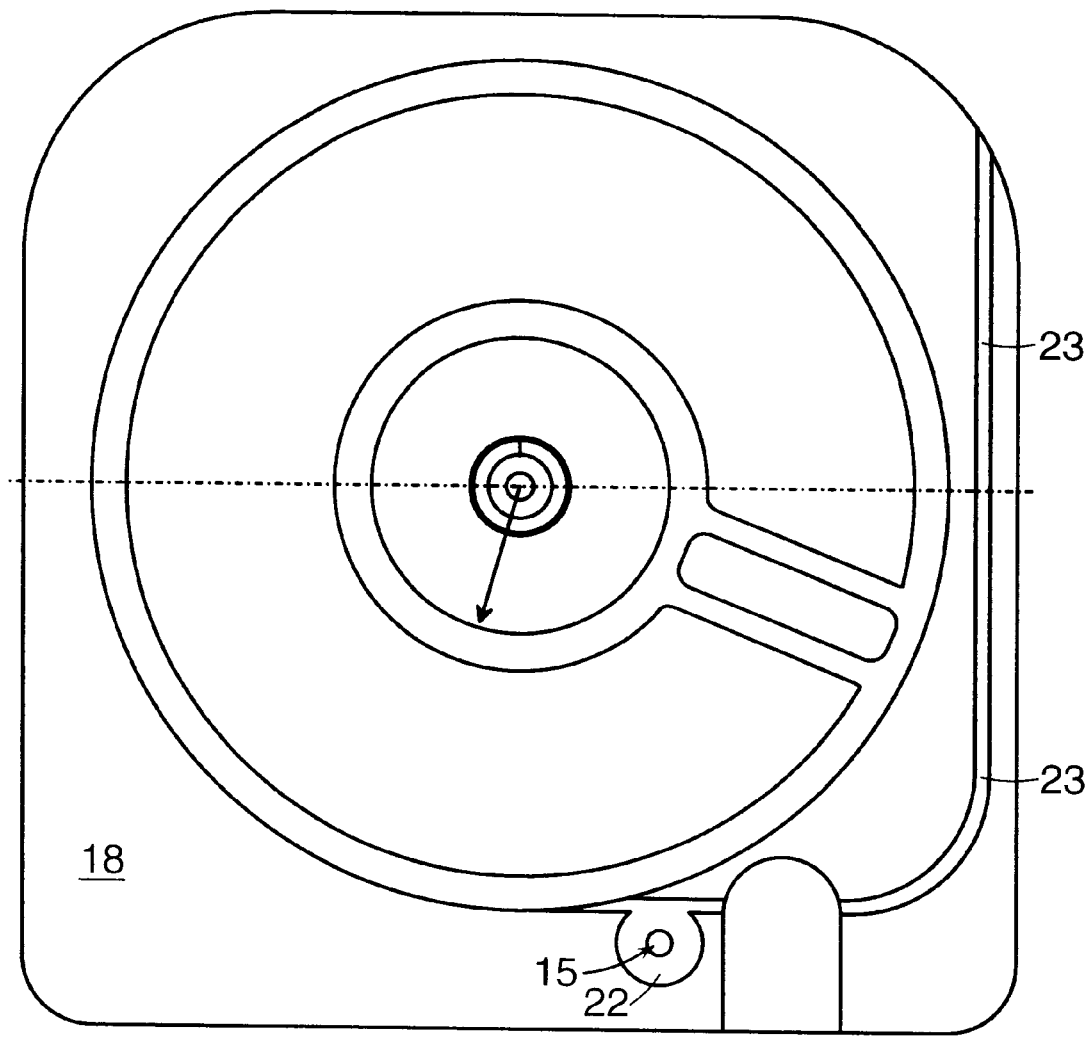
FIG. 10 is a top view of the housing according to a preferred embodiment.

A housing 18, according to a particular embodiment, is illustrated in FIG. 7 as is the catheter reel 5 to be held within the housing 18. Their assembly is shown in FIG. 8. The guidewire anchor 15 is affixed to the housing 18. FIG. 10 shows an embodiment wherein an anchor 15 may be placed in a bore 22 and made releasable and a slot 23 provided by the housing 18 holds additional guidewire 7 disposed distally from the lumen 6.

The housing preferably includes a fluid port to facilitate rinsing of the catheter 2 within the housing 18 with saline solution or an anticoagulant. Such rinsing is desirable if the catheter 2 has been withdrawn from the body location and is to be reinserted.

Referring again to FIG. 7, a distal end of a support for the portion of catheter 2 emerging from the housing 18 may be mounted to the housing 18 at the catheter exit 19. The support (not shown) may extend from the catheter exit 19 to a location at which the catheter 2 and the guidewire 7 (or second wire) enters the body of a patient. Such a support would reduce kinking or bending of the catheter 2 between the catheter exit 19 and the patient's body.

In order to limit the length of catheter that is paid out, a stop dog 20 and a stop dog groove 21 in the housing 18 may be provided, as shown in FIG. 7. These components are part of a payout limiter that restricts the number of rotations of the catheter reel 5 within the housing 18. Specific embodiments of the payout limiter are described below in connection with FIGS. 11–14.

Turning knob 24 deploys the catheter, beginning at proximal end 17, from the reel 5 out of the catheter exit 19. The guidewire 7 is anchored and constrained within guidewire groove 12. The distal end of the catheter is held and constrained in the reel. The continued rotation of the reel 5 effectively transfers guidewire portions which exit from the lumen because of continued catheter deployment from the second or catheter groove 13 to the first or guidewire groove 12. The grooves are shaped so that the catheter may move freely to the exit 19 with no backlash.

The guidewire 7 may be of sufficient length to guide the proximal end of the catheter 17 to the desired location. Alternatively, the operator may place the proximal terminus of a second wire at the desired location in the patient's body while retaining access to the second wire's distal terminus. A fastener (not shown) may also be provided to be placed at or near the proximal terminus of the guidewire in order to removably affix a second wire to the guidewire 7. Subsequently fastening guidewire 7 to the distal terminus of the second wire will result in the required catheter 2 movement from reel 10 to the location with sufficient reel rotation. Unfastening the guidewire 7 after catheter 2 withdrawal eases an exchange of catheters without moving the proximal terminus of the second wire.

Figure 9:
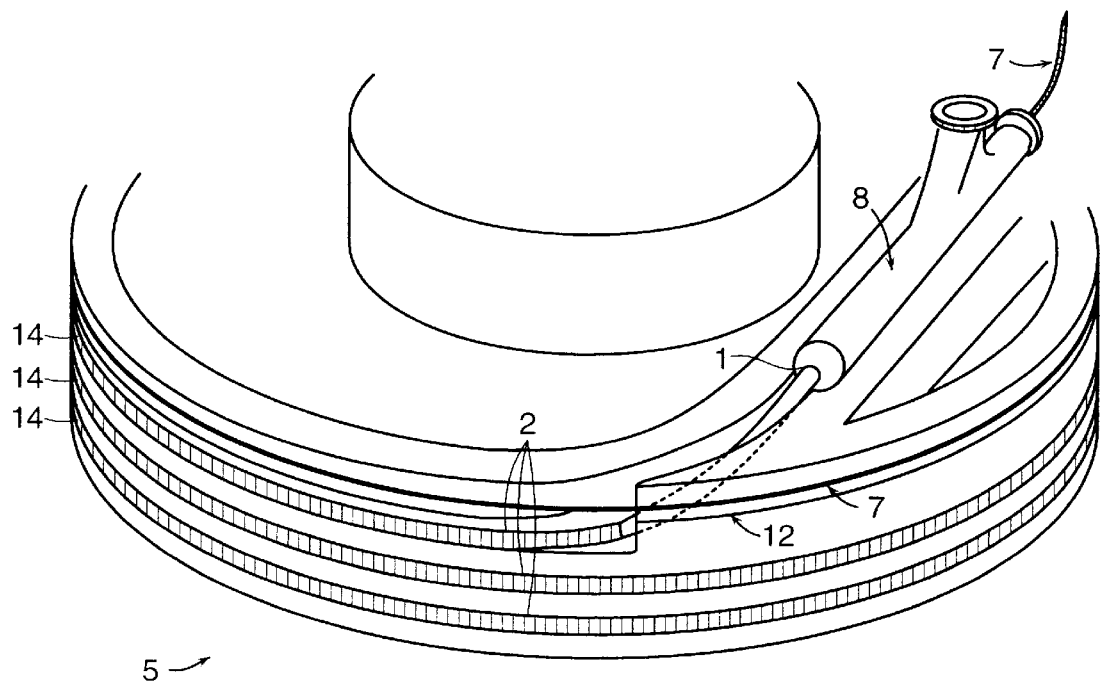
FIG. 9 illustrates a reel holding a catheter and a guidewire according to a preferred embodiment of the invention.

FIG. 9 shows, in accordance with a particular embodiment of the invention, the continuous helical second groove 14 in a perspective view. The figure also illustrates bending of the catheter 2 near its distal end 1 to direct the catheter 2 to occupy the second groove 14.

FIG. 10 is a top view of housing 18 in accordance with a specific embodiment. (Although reference is made to top and bottom views, it will be appreciated that the apparatus of the present invention can operate in any number of orientations.) A bore 22 is provided to facilitate access to and the function of a releasable guidewire anchor 15 (not shown). A slot 23, extending distally from the bore 22, is provided to hold additional guidewire 7.

Figure 11:
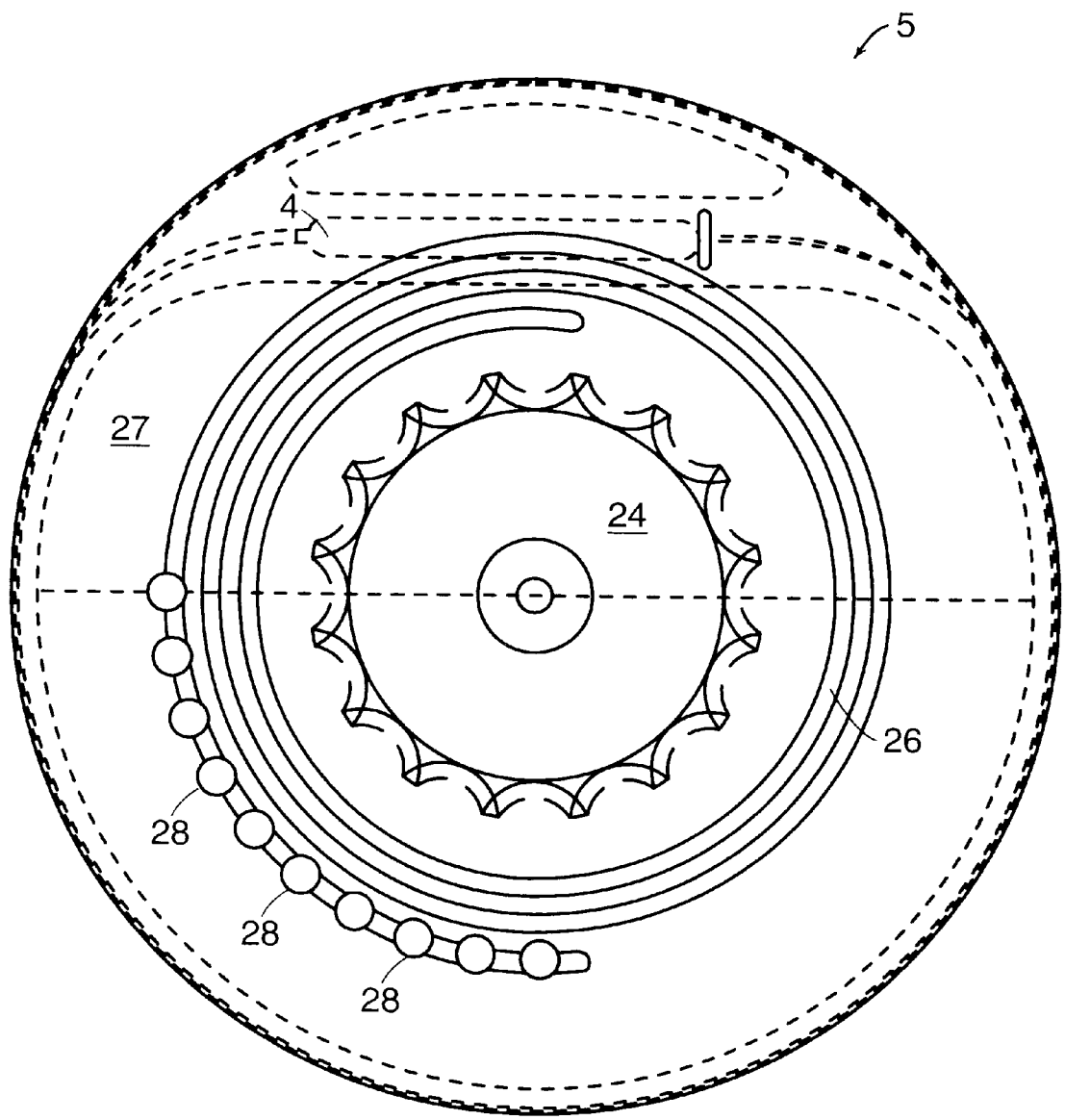
FIG. 11 is a bottom view of the catheter reel according to a preferred embodiment.
Figure 12:
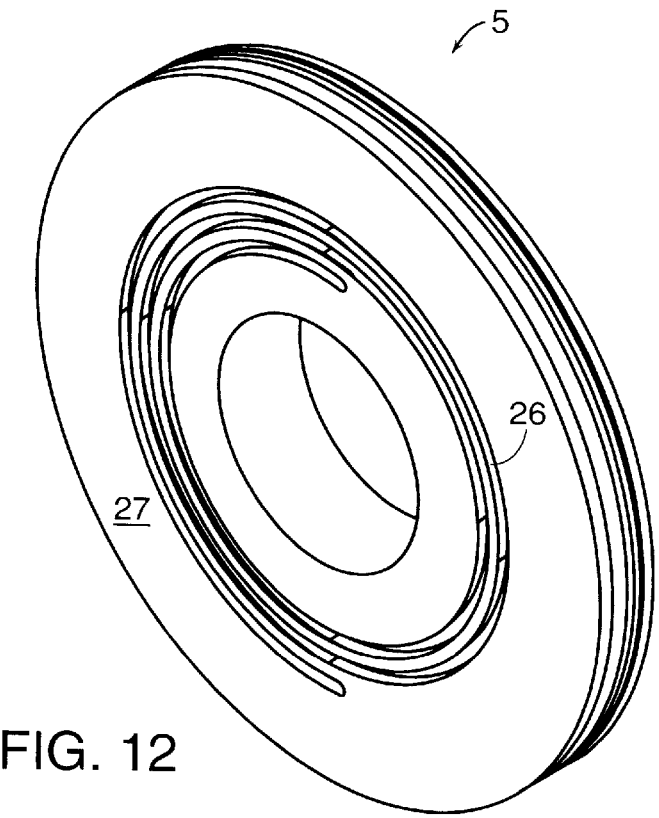
FIG. 12 is a perspective view of the catheter reel according to an alternative embodiment.
Figure 13:
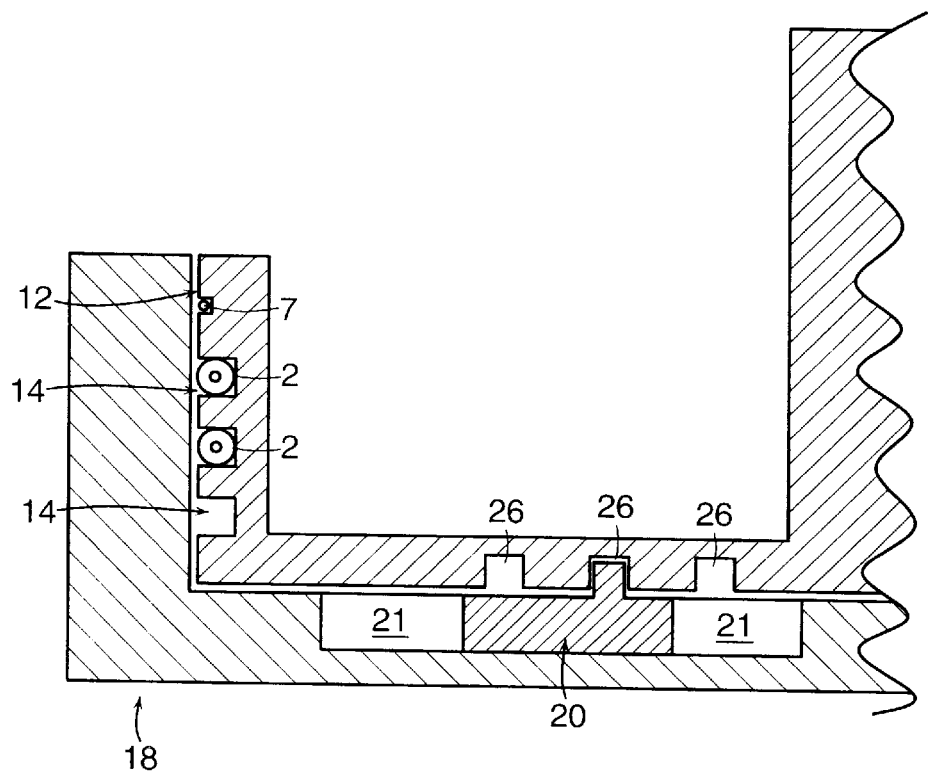
FIG. 13 is a cross-section view of an assembled catheter reel and housing according to a particular embodiment.
Figure 14:
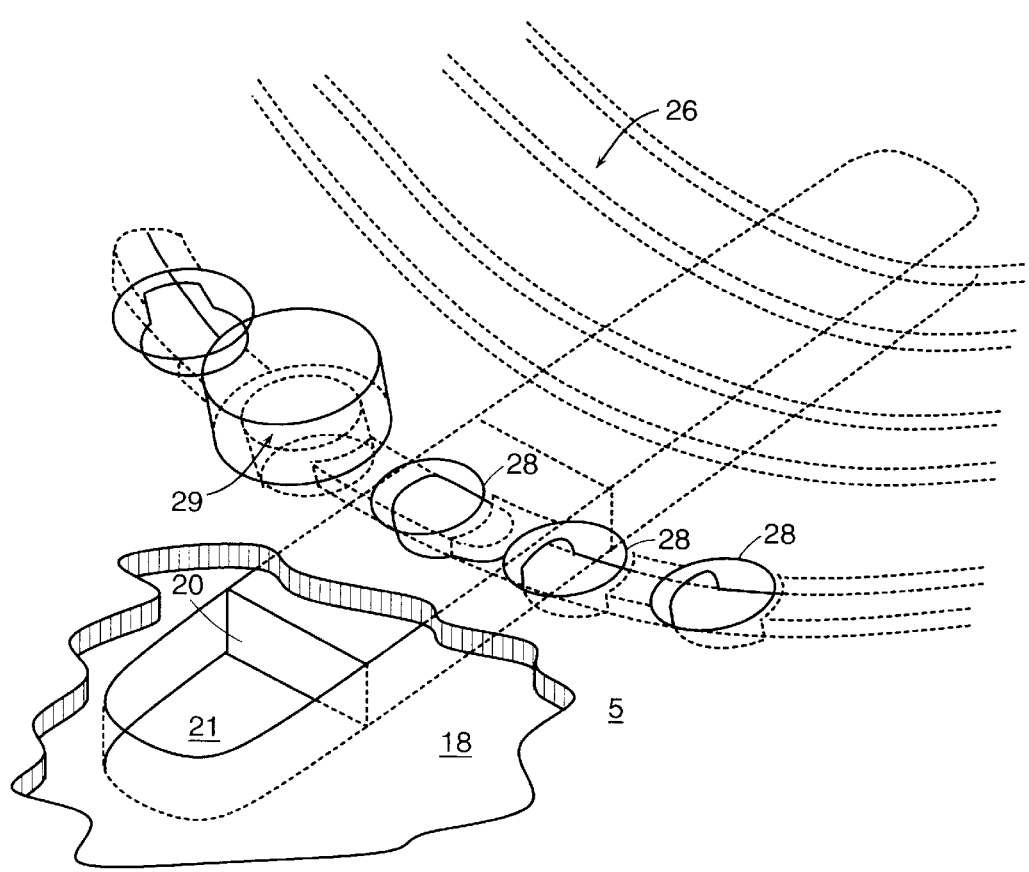
FIG. 14 is a top cutaway view of the assembled apparatus according to a specific embodiment.

Figures 11–14 illustrate specific embodiments of a catheter payout limiter. FIGS. 11 and 12 feature a spiral rotation-limiting groove 26 disposed on a bottom face 27 of the catheter reel 5. FIG. 13 is a representation of how a stop dog 20, seated in the stop dog groove 21 provided by the housing 18 is designed to engage the rotation—limiting groove 26. FIG. 11 additionally shows, in a particular embodiment of the invention, a series of stop-adjustment holes 28 provided by the catheter reel. The function of stop-adjustment holes 28 is illustrated in FIG. 14. A stop 29, sized to reside in a hole 28, makes contact with the stop dog 20 at a particular position. Further rotation of the catheter reel 5 in the withdrawing direction is thereby impeded. Different lengths of catheter 2 may be accommodated during manufacture of catheter reel 5 by moving stop 29 from a particular hole 28 to another hole 28. In a preferred embodiment, stop 29 is appropriately positioned and set in place during manufacture of catheter reel 5.

The present invention may be used with great advantage in a variety of situations and environments requiring the movement and handling of catheters. Moreover, although the invention has been described in detail with particular reference to specific embodiments thereof, it should be understood that the invention includes other and different embodiments. As is apparent to those skilled in the art, variations and modifications can be affected while remaining within the spirit and scope of the invention. The foregoing disclosure, descriptions and figures are only for illustrative purposes and do not, in any way, limit the invention which is defined only by the appended claims.

What is claimed is:

1. An apparatus for moving a catheter, having a proximal end, a distal end, and at least one lumen, along a guidewire, having a proximal terminus and a distal terminus, the apparatus comprising:

a reel, having an axis of rotation, and having a rim, the rim having a first groove for carrying a portion of the guidewire that lies outside the catheter and a second groove for carrying a portion of the catheter, wherein a portion of the guidewire lies within the portion of the catheter carried in the second groove; and a housing for holding the reel, the housing having an exit through which the catheter may pass.

2. The apparatus of claim 1 further comprising:

an arrangement for engaging the catheter with the reel; and an anchor, attached to the housing, for rigidly holding the distal terminus of the guidewire.

3. The apparatus of claim 2 wherein the housing defines a slot, located adjacent to the anchor, and extending away from the reel, to hold a portion of the guidewire.

4. The apparatus of claim 2, wherein the anchor is releasable to permit movement of the guidewire through the catheter while the reel is stationary with respect to the housing.

5. The apparatus of claim 2 wherein the arrangement for engaging the catheter is located in a connecting passage defined by the reel, the connecting passage having a proximal opening and a distal opening, the catheter extending outwardly from the proximal opening, the proximal opening oriented to permit the catheter to occupy the second groove, the distal opening oriented to permit the portion of the guidewire that lies outside the catheter to pass through the distal opening and to occupy the first groove.

6. The apparatus of claim 1 further comprising:

a support through which the catheter may pass, having a proximal end and a distal end, the distal end mounted to the housing at the exit.

7. The apparatus of claim 1 further comprising:

a fastener to removably affix a second wire to the guidewire, the fastener able to pass through a catheter lumen.

8. The apparatus of claim 1 wherein the housing has at least one fluid port permitting fluid communication with the reel.

9. The apparatus of claim 1 further comprising:

a payout limiter, restricting the number of rotations of the reel within the housing.

10. The apparatus of claim 1 wherein the reel has at least one face orthogonal to the rim, the apparatus further comprising:

a knob affixed to the face.

11. The apparatus of claim 1 wherein the guidewire carried in the first groove is located at the same distance from the axis of rotation as the guidewire carried in the second groove.

* * * * *